United States Patent
Potechin et al.

(10) Patent No.: US 9,504,635 B2
(45) Date of Patent: Nov. 29, 2016

(54) COMPOSITION CONTAINING 4-OXOVALERIC ACID AND LEUCONOSTOC/RADISH ROOT FERMENT FILTRAT

(71) Applicant: Colgate-Palmolive Company, New York, NY (US)

(72) Inventors: Kathy Potechin, Short Hills, NJ (US); Christine Boyke, Somerset, NJ (US)

(73) Assignee: Colgate-Palmolive Company, New York, NY (US)

( * ) Notice: Subject to any disclaimer, the term of this patent is extended or adjusted under 35 U.S.C. 154(b) by 30 days.

(21) Appl. No.: 14/503,429

(22) Filed: Oct. 1, 2014

(65) Prior Publication Data
US 2015/0017152 A1 Jan. 15, 2015

Related U.S. Application Data

(62) Division of application No. 13/810,851, filed as application No. PCT/US2010/042409 on Jul. 19, 2010, now Pat. No. 8,877,184.

(51) Int. Cl.
| | |
|---|---|
| A61Q 19/10 | (2006.01) |
| A61K 8/97 | (2006.01) |
| A61K 8/365 | (2006.01) |
| A61K 8/60 | (2006.01) |
| A61K 8/64 | (2006.01) |

(52) U.S. Cl.
CPC ............... *A61K 8/365* (2013.01); *A61K 8/602* (2013.01); *A61K 8/604* (2013.01); *A61K 8/64* (2013.01); *A61K 8/97* (2013.01); *A61Q 19/10* (2013.01); *A61K 2800/524* (2013.01); *A61K 2800/596* (2013.01); *A61K 2800/5922* (2013.01); *A61K 2800/77* (2013.01); *A61K 2800/85* (2013.01)

(58) Field of Classification Search
None
See application file for complete search history.

(56) References Cited

U.S. PATENT DOCUMENTS

| | | | |
|---|---|---|---|
| 3,793,210 | A | 2/1974 | Corey |
| 5,242,615 | A | 9/1993 | Urfer et al. |
| 5,370,816 | A | 12/1994 | Balzer et al. |
| 5,449,475 | A | 9/1995 | Cauwet et al. |
| 5,599,476 | A | 2/1997 | Behler et al. |
| 5,670,471 | A | 9/1997 | Amalric et al. |
| 5,916,575 | A | 6/1999 | McAtee et al. |
| 6,211,139 | B1 | 4/2001 | Keys et al. |
| 6,432,395 | B1 | 8/2002 | Rochon et al. |
| 6,491,928 | B1 | 12/2002 | Smith, III |
| 7,250,392 | B1 | 7/2007 | Leonard et al. |
| 7,396,808 | B1 | 7/2008 | Hood et al. |
| 7,414,016 | B1 | 8/2008 | van Buskirk et al. |
| 7,470,331 | B1 | 12/2008 | van Buskirk et al. |
| 2002/0037267 | A1 | 3/2002 | Guillou et al. |
| 2003/0069148 | A1 | 4/2003 | Booker et al. |
| 2003/0069161 | A1 | 4/2003 | Lee et al. |
| 2003/0134761 | A1 | 7/2003 | Sebillotte-Arnaud et al. |
| 2004/0136940 | A1 | 7/2004 | Lazarowitz |
| 2007/0048235 | A1 | 3/2007 | Harmalker et al. |
| 2008/0157754 | A1 | 7/2008 | Kim et al. |
| 2008/0318822 | A1 | 12/2008 | Ochomogo et al. |
| 2008/0318831 | A1 | 12/2008 | Hood et al. |
| 2009/0023620 | A1 | 1/2009 | Ochomogo et al. |
| 2009/0036339 | A1 | 2/2009 | Sans et al. |
| 2010/0129305 | A1* | 5/2010 | Lee .......................... A61K 8/31 424/63 |

FOREIGN PATENT DOCUMENTS

| | | |
|---|---|---|
| DE | 4319700 | 12/1994 |
| DE | 19916335 | 10/2000 |
| DE | 102004033206 | 2/2006 |
| EP | 0044262 | 9/1991 |
| EP | 0555086 | 8/1993 |
| EP | 1284135 | 2/2003 |
| EP | 1702609 | 9/2006 |
| JP | 2002-326918 A * | 11/2002 |
| JP | 2009 191019 | 8/2009 |
| WO | WO 97/47171 | 12/1997 |
| WO | WO 03/028694 | 4/2003 |
| WO | WO 2007/127987 | 11/2007 |
| WO | WO 2008/015186 | 2/2008 |
| WO | WO 2009/023010 | 2/2009 |
| WO | WO 2009/029046 | 3/2009 |
| WO | WO 2010/106417 | 9/2010 |

OTHER PUBLICATIONS

Yamada et al. (2002-326918A, English translation).*
Fiedler, et al., 2002, "Fiedler Encyclopedia of Excipients for Pharmaceuticals, Cosmetics and related areas," editio Cantor Verlag, Aulendorf, vol. 2, pp. 1219-1220 (XP002644333).
Gottschalck, et al., 2008, "Leuconostoc/Radish Root Ferment Filtrate," International Cosmetic Ingredient Dictionary and Handbook. 12th Edition, The Cosmetic, Toiletry and Fragrance Association, Washington, DC, vol. 2, p. 1453 (XP002658680).
Gottschalck, et al., 2008, "Levulinic Acid," International Cosmetic Ingredient Dictionary and Handbook 12th Edition, The Cosmetic, Toiletry and Fragrance Association, Washington, DC, vol. 2, p. 1454 (XP002658681).
Cognis: "Product Data Sheet Plantaren 2000 N UP (Rev. 15.1)", Retrieved from the Internet: URL:http://www.products.cognis.com/cognis/prodleaf.nsf/($ProductsbyDocID_PL-Header)/REFF54F84FEBFCF027485256AD3006B003E/$file/PLANTAREN_r_2000_N_UP_E.pdf (retrieved on Jun. 22, 2011) (XP002644337).
Safety Data Sheet for Dermosoft™ 700B, Feb. 26, 2008.
Dermosoft™ 700B Product Information, Jan. 2008, undated.
Multifunctional Cosmetic Additives from drstraetmans, undated.
MSDS—Leucidal™ Liquid, Mar. 17, 2110.
A 'Natural' Preservative from Active Micro Systems, http://www.happi.com/articles/2008/07/gleams-notion, downloaded Apr. 13, 2010.

(Continued)

*Primary Examiner* — Karen Cochrane Carlson
*Assistant Examiner* — Jennifer M. H. Tichy

(57) ABSTRACT

A composition comprising 4-oxovaleric acid present in an amount of 0.05 to 1% by weight (as supplied) of the composition and *leuconostoc*/radish root ferment filtrate present at 0.2 to 2% by weight (as supplied) of the composition.

14 Claims, No Drawings

(56) References Cited

OTHER PUBLICATIONS

Natural Preservative—Leneidal Liquid, http://theherbarie.com/Leucidal-Liquid-pr-439.html, downloaded Apr. 13, 2010.
International Search Report issued for corresponding International Application No. PCT/US2010/042409 mailed Oct. 7, 2011.
Escentials of Australia Pty Ltd, Cosmetic Ingredients, "Decyl Glucoside," 2003, Retrieved online: <URL:https:www.escentialsofaustralia.com/php/product_listing.php?gid=76>.
Josef Koester, Cognis Green Chemical Solutions™, Oct. 27, 2009, Retrieved online: <URL:http://www.midwestsee.org/archives/SCC_Cognis_Green_Solution_102709.pdf>.

* cited by examiner

COMPOSITION CONTAINING 4-OXOVALERIC ACID AND LEUCONOSTOC/RADISH ROOT FERMENT FILTRAT

CROSS REFERENCE TO RELATED APPLICATIONS

This application is a divisional application of application Ser. No. 13/810,851 filed on 17 Jan. 2013, which is a national stage entry of PCT/US2010/042409, filed on 19 Jul. 2010, all of which are incorporated herein by reference.

BACKGROUND

For consumers who use liquid cleansing compositions, such as shower gels, body washes, or liquid hand soaps, foaming of the cleansing composition during use is desired. Also, it is desired to provide a sufficient amount of foam that is stable for a desired amount of time during use. Also, there is a desire for the foam to provide a creamy texture. The foam volume and creaminess usually compete against each other. As one is increased, the other one usually decreases. It is desired to provide a cleansing composition with a desired amount of foam and a desired amount of creaminess.

BRIEF SUMMARY

A composition comprising 4-oxovaleric acid present in an amount of 0.05 to 1% by weight (as supplied) of the composition and *leuconostoc*/radish root, ferment filtrate present at 0.2 to 2% by weight (as supplied) of the composition.

DETAILED DESCRIPTION

As used throughout, ranges are used as a shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

Typically, anionic surfactants are used to provide foaming characteristics to compositions. Other types of surfactants may not generate as much or the same quality of foam as does anionic surfactants. It is been discovered that a combination of decyl and coco glucosides can provide foaming that is comparable to anionic surfactants. In certain embodiments, anionic surfactants can be eliminated from the composition, but the composition can still have a desired level of foaming.

A cleansing composition that includes surfactants comprising decyl glucoside and coco glucoside, wherein the amount of decyl glucoside is 1.5 to 2.5, 1.8 to 2.2, or 1.9 to 2.1 times the amount of coco glucoside by weight. In certain embodiments, the amount of decyl glucoside is about 2 times the amount of coco glucoside.

The decyl glucoside and the coco glucoside can be included in the composition in any amount as long, as the weight ratio is maintained. In certain embodiments, the amount of decyl glucoside is 1 to 30 weight %, 1 to 20 weight %, or 10 to 20 weight % of the composition. In certain embodiments, the amount of decyl glucoside is 20, 15, or 10 weight %. In certain embodiments, the amount of coco glucoside is 0.5 to 20 weight %, 0.5 to 10 weight % or 5 to 10 weight % of the composition. In certain embodiments, the amount of coco glucoside is 10, 7.5, or 5 weight %.

The decyl and coco glucoside surfactants can be obtained from Cognis Corporation. The coco glucoside is sold as Plantacare™ 818 UP. The decyl glucoside is sold as Plantaren™ 2000 N UP.

In certain embodiments, the cleansing composition can contain a thickener. Examples of the thickener include, but are not limited to xanthan gum, konjac mannan, gellan gum, carrageenan, carboxymethyl cellulose, guar gum, rhamsan gum, furcelloran gum, celluloses, polysaccharides, pectin, alginate, and arabinogalactan. In one embodiment, the thickener is xanthan gum. In another embodiment, the thickener is kontac mamma. In certain embodiments, the thickener is present in an amount alone or in combination of 0.1 to 5% by weight, 0.25 to 2% by weight, 0.75 to 1.5 by weight, or 1 to 1.25% by weight.

The cleansing composition contains water. Water can be present in any desired amount of the cleansing composition to form a typical cleansing composition, such as it shower gel, a body wash, liquid hand soap, or foaming hand soap.

The cleansing composition can contain additional surfactants. In certain embodiments, the surfactants can consist essentially of the decyl and coco glucosides, or the surfactants can consist of the decyl and coco glucosides. In certain embodiments, the total amount of surfactant can be 1 to 45% by weight of the composition.

Additionally, the cleansing composition can contain any other materials that can be included in a cleansing composition. Examples of additional surfactants and other materials can be found in United States Patent Publication No. 20070048235. The pH of the composition can be adjusted with citric acid.

In the examples below, the compositions contain a combination of Dermosoft™ 700B perfume and Leucidal™ leticonostoc/radish root ferment filtrate as preservative. The amounts listed are the weight of the material as supplied. The Dermosoft™ 700B perfume can be included in an amount of 0.05 to 1 or 0.3 to 1 by weight of the composition (as supplied). The Leucidal™ *leuconostoc*/radish root ferment filtrate can be included in an amount of 0.2 to 2% by weight of the composition (as supplied). In one embodiment, Dermosoft™ 700B perfume is present in an amount of about 0.3 by weight (as supplied) of the composition and the Leucidal™ *lenconostoc*/radish root ferment filtrate is present at about 1.25% by weight (as supplied) of the composition. The combination provides preservative protection against gram positive bacteria, grain negative bacteria, mold, yeast, and fungus. The Leucidal™ *lenconostoc*/radish root ferment filtrate is available from Active Concepts LLC, and the Dermosoft™ 700B is available from Dr. Straetmans Chemische Produkte GmbH.

According to the MSDS for Dermosoft™ 700B, the material is about 40% by weight of a partially neutralized 4-oxovaleric acid, in glycerin and water. When the composition is used at 0.05 to 1% by weight in a composition, the active amount of 4-oxovaleric acid is 0.02 to 0.4 by weight.

In other embodiments, the Dermosoft™ 700B can be used alone, the Leucidal™ *leuconostoc*/radish root ferment filtrate can be used alone, or other preservatives can be used alone or in combination with these preservatives.

In another embodiment, the compositions can be opacified by including an opacifier, such as sunflower oil or Euperlan™ Green opacifier from Cognis (55-65% water, 15-25% lauryl glucoside and 15-25% stearyl citrate). The opacifier can be present in an amount of 1 to 5% by weight of the composition. In certain embodiments, the sunflower oil is present at 1 to 5 or 2 to 4% by weight of the composition. In certain embodiments, the amount is about 3% by weight of the composition. In certain embodiments, the Euperlan™ Green opacifier is present at 1 to 5 or 2 to 4% by weight of the composition. In certain embodiments, the amount is about 3% by weight of the composition.

In certain embodiments, the cleansing composition can contain a chelator. Examples of a chelator include, but are not limited to sodium phytate and tetrasodium EDTA. In certain embodiments, the chelator is present in an amount of 0.001 to 3% by weight, 0.01 to 1:5% by weight, or 0.05 to 1.0% by weight of the composition.

In certain embodiments, the materials in the composition can be obtained from naturally occurring sources that are sustainable. This provides a composition that performs comparably to some anionic surfactant based cleansing compositions yet is made from sources of raw materials that are naturally occurring from sustainable sources.

The cleansing composition can be formulated to be in the form of a shower gel, body wash, liquid hand soap, or foaming, hand soap.

In some embodiments the pH of the composition is 2 to 9. In one embodiment, the pH of the composition is 3 to 7. In other embodiments, the pH of the composition is 4 to 6. In another embodiment the pH of the composition is 6 to 8. The pH is measured at 25° C., In some embodiments, the composition has a Brookfield viscosity of 1 to 25,000 mPas (cps). In one embodiment, the viscosity is less than 15,000 mPas (cps). In other embodiments, the viscosity is 5000 to 12,000 mPas (cps). Brookfield viscosity is measured on a DVII viscometer with spindle 4 at 10 rpm at 25° C. In another embodiment the viscosity is 1 to 100 mPas (cps) using spindle 3 at 100 rpm at 25° C.

Compositions may be made using conventional mixing techniques known to those skilled in the art for mixing ingredients.

Specific Embodiments

The examples are merely illustrative and do not in any way limit the scope of the invention as described and claimed. In the examples below, all of the ingredients are obtained from a natural, sustainable source.

The following examples and comparative examples can be prepared by mixing of the ingredients. The amounts are in weight Water is added to a vessel equipped with center turbine agitation. Citric acid (50% solution) is added to the water and mixed until homogeneous. Xanthan gum is slowly added to the water solution while mixing at high speed. Once all the xanthan has been uniformly dispersed and the solution is clear, the decyl glucoside is slowly added to batch at medium speed until homogeneous. Coco-glucoside is added slowly to the batch at medium speed and mixed until homogeneous. Glycerin, salt, preservatives, and skin feel enhancers (if necessary) are added to the batch in succession mixing until homogeneous in between components. pH and viscosity are measured and adjusted if necessary.

The following samples are prepared for testing by an expert panel. The compositions are compared against as body wash with anionic surfactants available as Softsoap™ Pomegranate and Mango body wash from Colgate-Palmolive company. This comparative composition is about 13.7% sodium lauryl ether sulfate (70% active), about 5.7% cocoamidopropyl betaine, about 1% xanthan gum, with the balance being water, preservative, fragrance, and color.

| Material | Example 1 | Example 2 |
|---|---|---|
| Decyl glucoside Plantaren ™ 2000 NUP | 10 | 20 |
| Coco glucoside Plantacare ™ 818 UP | 5 | 10 |
| Xanthan gum | 1.0 | 1.0 |
| Glycerin | 2.5 | 2.5 |
| Sodium chloride | 1.5 | 1.5 |
| Dermosoft ™ 700B perfume (4-oxovaleric acid) (preservative) | 0.6 | 0.6 |
| Water and minors, such as fragrance, color, pH adjustment | Q.S. | Q.S. |
| Total | 100 | 100 |

The compositions are evaluated by 9 expert panelists. Each panelist assesses each product using a standardized methodology and a 0-15 point scale, 0 representing the none/low and 15 representing a high. The expert panel evaluates the products on sensory characteristics including: Visual product appearance, foam evaluation on pouf and hand.

For visual evaluation, the panelist dispenses each test product from its original package using a 3-second consistent squeeze onto a transparency. The panelist then evaluates the test products on Integrity of Shape immediately and after 1 minute.

There are two phases of assessment on lather—lather generated on pouf and lather generated on hands. The panelists evaluated such attributes as Amount of foam on pouf, firmness of foam and amount of foam on hands. For Pouf Evaluation Procedure, the panelist weighs 3.0 g±0.1 g onto a tray. The panelist completely submerges the pouf in 33° C.±1 (92° F.±2) water for 5 seconds and then removes pouf. The panelist then adds the product from the tray onto the pouf, twists the pouf 10 times, and then evaluates lather attributes. For Hand Evaluation Procedure, the panelist weighs out 2.0 g±0.1 g onto a tray. The panelist wets both hands under running water at 33° C.±1 (92° F.±2) for 5 seconds, then dispenses the test product from the tray onto the non-dominant hand, and adds 2.5 ml±0.1 ml of water. The panelist then uses a gentle circular motion rotating 10 times in the hand to generate lather and subsequently evaluates the lather attributes.

An analysis of variance (ANOVA) is performed on the panelists ratings of product attributes; a within subject model was used. A Tukey HSD is used to evaluate significant differences among the attributes ($p<0.10$; two tailed). The results from the expert panel are below.

| | P-value | 10/5 Prototype Example 1 A | 20/10 Prototype Example 2 B | Softsoap Pomegranate C |
|---|---|---|---|---|
| | | VISUAL EVALUATION: | | |
| Integrity of Shape - Immediate | <.0001 | 8.0 | 8.0 | 8.0 |

-continued

|  | P-value | 10/5 Prototype Example 1 A | | 20/10 Prototype Example 2 B | | Softsoap Pomegranate C | |
| --- | --- | --- | --- | --- | --- | --- | --- |
| Integrity of Shape - 1 minute | <.0001 | 7.0 | | 7.0 | | 7.0 | |
| POUF EVALUATION: | | | | | | | |
| Amount of Foam-5T | <.0001 | 4.4 | | 4.2 | | 4.2 | |
| Amount of Foam-10T | <.0001 | 9.0 | BC | 8.2 | A | 8.3 | A |
| Firmness of Foam-10T | <.0001 | 2.1 | B | 1.6 | A | 2.0 | B |
| HAND EVALUATION: | | | | | | | |
| Amt Foam-Hands-5T | <.0001 | 2.0 | | 1.9 | | 2.0 | |
| Amt Foam-Hands-10T | 0.0022 | 4.0 | | 3.9 | | 4.0 | |

It can be seen that the glucoside containing compositions perform similarly to the anionic containing surfactant composition.

The formulas below are for opacified versions of Examples 1 and 2.

| Material | Example 3 | Example 4 |
| --- | --- | --- |
| Decyl glucoside Plantaren ™ 2000 NUP | 10 | 20 |
| Coco glucoside Plantacare ™ 818 UP | 5 | 10 |
| Xanthan gum | 1.0 | 1.0 |
| Glycerin | 2.5 | 2.5 |
| Sodium chloride | 1.5 | 1.5 |
| Dermosoft ™ 700B perfume (4-oxovaleric acid) (preservative) | 0.6 | 0.6 |
| Sunflower oil (opacifier) | 3 | 3 |
| Water and minors, such as fragrance, color, pH adjustment | Q.S. | Q.S. |
| Total | 100 | 100 |

The formula below is for a foaming liquid hand soap.

| Material | Example 5 |
| --- | --- |
| Decyl Glucoside | 10 |
| Coco Glucoside | 5 |
| Dermosoft ™ 700B perfume (4-oxovaleric acid) (preservative) | 0.3 |
| Leucidal ™ leuconostoc/radish root ferment filtrate (preservative) | 1.25 |
| Water and minors, such as fragrance, color, pH adjustment | Q.S. |
| Total | 100 |

Below is a prophetic example.

| Material | Ex. 6 |
| --- | --- |
| Decyl glucoside:coco glucoside ratio | 2:1 |
| Decyl glucoside Plantaren ™ 2000 NUP | 10-20 |
| Coco glucoside Plantacare ™ 818 UP | 5-10 |
| Xanthan gum | 1-1.25 |
| Glycerin | 3 |
| Sodium chloride | 1.5 |
| Dermosoft ™ 700B perfume (4-oxovaleric acid) (preservative) | 0.3 |
| Leucidal ™ leuconostoc/radish root ferment filtrate (preservative) | 1.25 |
| Water and minors, such as fragrance, color, pH adjustment | Q.S. |
| Total | 100 |

What is claimed is:

1. A cleansing composition comprising:
   a) a partially neutralized 4-oxovaleric acid present in an amount of 0.02 to 0.4% by weight of the composition,
   b) *leuconostoc*/radish root ferment filtrate present in an amount of 0.2 to 2% by weight of the composition, wherein the *leuconostoc*/radish root ferment filtrate is derived from radishes fermented with *Leuconostoc kimchii*, a lactic acid bacteria,
   c) at least one surfactant present in an amount of 1 to 45% by weight of the composition, and
   d) water,
      wherein the combination of the partially neutralized 4-oxovaleric acid and *leuconostoc*/radish root ferment filtrate provides preservative protection against gram positive bacteria, gram negative bacteria, mold, yeast and fungus.

2. The cleansing composition of claim 1, wherein the partially neutralized 4-oxovaleric acid is present in an amount of about 0.12% by weight of the composition and the *leuconostoc*/radish root ferment filtrate is present at about 1.25% by weight of the composition.

3. The cleansing composition of claim 1, wherein the at least one surfactant is free of an anionic surfactant.

4. The cleansing composition of claim 1, wherein the at least one surfactant comprises a combination of decyl glucoside and coco glucoside.

5. The cleansing composition of claim 1, further comprising at least one of a thickener and an opacifying agent.

6. The cleansing composition of claim 5, wherein the opacifying agent is sunflower oil or a composition comprising 55-65% water, 15-25% lauryl glucoside and 15-25% stearyl citrate.

7. The cleansing composition of claim 6, wherein the opacifying agent is present in an amount of 1 to 5% by weight of the composition.

8. The cleansing composition of claim 1, further comprising a chelator.

9. The cleansing composition of claim 8, wherein the chelator is sodium phytate or tetrasodium EDTA.

10. The cleansing composition of claim 8, wherein the chelator is present in an amount of 0.001 to 3%.

11. The cleansing composition of claim 4, further comprising a chelator.

12. The cleansing composition of claim 1, further comprising a chelator, a thickener and an opacifying agent.

13. The cleansing composition of claim 12, wherein the opacifying agent is sunflower oil or a composition comprising 55-65% water, 15-25% lauryl glucoside and 15-25% stearyl citrate, wherein the opacifying agent is present in an amount of 1 to 5% by weight of the composition, wherein the chelator is sodium phytate or tetrasodium EDTA, and wherein the chelator is present in an amount of 0.001 to 3%.

14. The cleansing composition of claim 1, wherein the cleansing composition is in the form of a shower gel, body wash, liquid hand soap, or foaming, hand soap.

* * * * *